United States Patent [19]

Grimm et al.

[11] 4,071,554

[45] Jan. 31, 1978

[54] METHOD FOR THE PREPARATION OF N,N-DIALKYL HYDRAZIDES

[75] Inventors: Robert A. Grimm, Columbus, Ohio; Neil A. Randen, Stillwater, Minn.; Christopher L. Demas, Columbus, Ohio

[73] Assignee: Ashland Oil, Inc., Ashland, Ky.

[21] Appl. No.: 718,223

[22] Filed: Aug. 27, 1976

Related U.S. Application Data

[63] Continuation-in-part of Ser. No. 559,806, March 19, 1975, abandoned.

[51] Int. Cl.² .................. C07C 109/087; C07C 109/10
[52] U.S. Cl. ........................... 260/558 H; 260/559 H; 260/561 H
[58] Field of Search ........... 260/558 H, 561 H, 559 H

[56] References Cited

U.S. PATENT DOCUMENTS

| | | | |
|---|---|---|---|
| 3,065,265 | 11/1962 | Gutmann et al. | 260/558 H X |
| 3,795,678 | 3/1974 | Bollag et al. | 260/558 H X |
| 3,965,174 | 6/1976 | Malz, Jr. et al. | 260/561 H |
| 4,045,484 | 8/1977 | Malz, Jr. et al. | 260/561 H |

FOREIGN PATENT DOCUMENTS

| | | | |
|---|---|---|---|
| 659,441 | 3/1963 | Canada | 260/558 H |
| 636,613 | 2/1962 | Canada | 260/558 H |

OTHER PUBLICATIONS

Biel et al., J. Am. Chem. Soc., vol. 81, pp. 2805–2806, (1959).

*Primary Examiner*—Daniel E. Wyman
*Assistant Examiner*—Thomas A. Waltz
*Attorney, Agent, or Firm*—William Kammerer

[57] ABSTRACT

A method for the preparation of N,N-dialkyl derivatives of mono- and diacyl hydrazines wherein the corresponding unsubstituted acid hydrazide is reductively alkylated with an aldehyde.

6 Claims, No Drawings

METHOD FOR THE PREPARATION OF N,N-DIALKYL HYDRAZIDES

CROSS REFERENCE TO RELATED APPLICATION

This application is a continuation-in-part of application Ser. No. 559,806, filed Mar. 19, 1975, now abandoned.

BACKGROUND OF THE INVENTION

1. Field of the Invention

This invention relates to a process for the N,N-alkylation of unsubstituted acid hydrazides.

2. Description of the Prior Art

The N,N-dialkyl acid hydrazides afford a potentially attractive way for preparing aminimides; i.e., those compounds characterized in having one or more

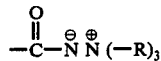

groups. The aminimides have recognized utility as surface active compounds, antimicrobial agents, polymerization catalysts, etc., as well as being precursors for deriving corresponding isocyanates in accordance with a known thermolytic rearrangement mechanism. The methods heretofore available for preparing aminimides, however, all involve the use of unsymmetrical disubstituted hydrazine as a reactant. On the other hand, the only commercially feasible method for preparing the latter hydrazines involves the hydrogenation of a nitroso secondary amine in turn obtained by nitrosating the 2° amine. These nitroso compounds have proven to be very potent carcinogens and consequently this method for the production of the indicated hydrazines stands currently abandoned. Accordingly, there presently exists an important need for a method of preparing aminimides which obviates the requirement for using an N,N-dialkyl hydrazine as a basic raw material.

SUMMARY OF THE INVENTION

In accordance with the present invention a method is provided for the preparation of an N,N-dialkyl acid hydrazide of the formula:

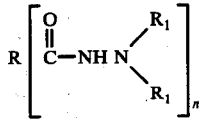

wherein $n$ is the integer 1 or 2; R is alkylene, m-phenylene or p-phenylene when $n$ is 2; R is alkyl or aryl when $n$ is 1; and $R_1$ is $C_1$–$C_6$ alkyl.

The method comprises first reacting hydrazine and a lower alkyl ester of a mono- or dicarboxylic acid having the formula $R(COOH)_n$ wherein R and n are as defined above, to form the corresponding acyl or diacyl hydrazine. The aforesaid mixture is thereupon reductively alkylated with a $C_1$–$C_6$ saturated aliphatic aldehyde to result in the formation of the N,N-dialkyl acid hydrazide.

DESCRIPTION OF THE PREFERRED EMBODIMENTS

The first step contemplated in the practice of the present invention involves the reaction of a lower alkyl ester of a mono- or dicarboxylic acid with hydrazine to form the corresponding acyl hydrazine. While this reaction is not new, in overall context of this invention the step represents an important integral aspect thereof inasmuch as it has been found that the acyl hydrazine as produced in the crude form can be reductively alkylated if the latter reaction is carried out in a particular manner, details concerning which will be given later. The reductive alkylation has been found to be a highly sensitive reaction mechanism and consequently it was surprising to find that crude acyl hydrazine could be employed as such without resorting to recrystallization procedures in order to obtain a pure form thereof.

The preparation of the acyl hydrazine consists of reacting the lower alkyl ester of the starting acid, preferably the ethyl ester, with hydrazine on an essentially equivalent basis. Preferably an excess of the ester is used ranging up to about 15% over the equivalent requirement. The reaction can be carried out in a lower alkanol of which methanol is most suitable. However, solvents are not necessary for effecting this reaction since the generated alcohol in combination with the associated water of the preferred form of the hydrazine serves to solubilize the reaction system in most instances. The hydrazine can be anhydrous but for economic reasons the conventional 85% hydrazine hydrate of commerce is preferred. An applicable reaction temperature range is from about 50° to 120° C. at atmospheric or moderately elevated pressure conditions. An alcohol solvent when employed is ordinarily used on the basis of about 1 mole per mole of the ester. The reaction mixture is maintained under the conditions indicated until there has been an almost quantitative utilization of the hydrazine.

A variety of saturated mono- and dicarboxylic acids can be utilized for deriving the substituted acid hydrazides contemplated herein. An enumeration of suitable monobasic acids include: acetic, propionic, caproic, caprylic, capric, lauric, myristic, palmitic, stearic, eicosanoic, behemic, carnaubic, etc. Representative of applicable saturated aliphatic dibasic acids are such as adipic, suberic, azelaic and sebacic. Of the aromatic acids, benzoic, meta- and terphthalic are representative.

Before proceeding with the reductive alkylation phase of the process, it is important that the crude acyl hydrazine be adjusted so as to exhibit a pH not in excess of 7.5. The preferred pH range is in the order of from 6 to 7. Maintaining the pH as indicated is one factor which allows the use of the crude acyl hydrazine. Additionally, pH control in this manner importantly contributes to extended catalyst life. The pH of the system can be regulated by the addition of an appropriate amount of a lower carboxylic acid such as, for example, formic, acetic acid or the anhydride thereof. Still another suitable acid for this purpose is phoshoric which can be most advantageously used under those circumstances where corrosion problems associated with the use of the indicated carboxylic acids are presented.

The next step in sequence consists of reductively alkylating the acidified crude acyl hydrazine with a $C_1$–$C_6$ saturated aliphatic aldehyde. This reaction is carried out by first adding the hydrogenation catalyst, pressuring with hydrogen, heating to the contemplated temperature and thereupon adding the aldehyde. The manner required for introducing the aldehyde is critical from the standpoint of obtaining optimum yield and for avoiding premature inactivation of the catalyst. The aldehyde is to be added slowly and continuously during this phase of the process. The time required for introducing the aldehyde can not be stated in absolute terms inasmuch as such depends on batch size and also on the reactor's design; e.g., agitation rate and ability to dissipate the rather considerable heat of reaction. In a large scale operation the addition rate of the aldehyde can be suitably arrived at simply by introducing this reactant at a rate which permits control of the temperature within the range specified. Normally in a plant or pilot plant type run the addition of the aldehyde can be accomplished within from 4 to 6 hours. The important factor to observe is that the aldehyde addition be continuous with continuous flow of the hydrogen throughout the reductive alkylation reaction. Any stoppage of the aldehyde addition can have a pronounced adverse effect upon catalyst activity resulting in a lower yield of the desired product.

As indicated, the applicable aldehydes include the $C_1$-$C_6$ saturated aliphatic type which is desirably employed as a solution in a lower alkanol. When formaldehyde is used as the aldehyde such can take the form of an aqueous or methanolic solution thereof. The preferred form of formaldehyde is Methyl Formcel (formaldehyde methyl hemiacetal). Irrespective of the specific aldehyde employed or the particular form thereof, it is desirably modified by the addition of acetic acid. The presence of the added acid serves to keep the reductive alkylation mixture within the proper pH range during the course of reaction. An amount of acetic acid in the order of about 4–6 wt. percent based on the aldehyde is adequate for this purpose. As indicated previously, other acids can be used; however, acetic acid is preferred. The amount of aldehyde suitable for conducting the reductive alkylation reaction is from 2 to 3 moles thereof per equivalent of the acyl hydrazine sought to be alkylated. The preferred combining ratio of the aforesaid reactants is about 2.1 moles of the aldehyde per equivalent of acyl hydrazine.

A suitable temperature range for carrying out the reductive alkylation reaction is from about 40° C. to 100° C. More preferably, the reaction temperature is maintained within the range of from about 60° to 85° C. During the reaction hydrogen pressures between about 7 and 17 atmospheres are generally applicable. Preferred pressure conditions are in the range of 8 to 10 atmospheres. Following the completion of the reaction, recovery of the resultant 1,1-dimethyl-2-acyl hydrazine can be accomplished by stripping the reaction mixture to remove volatiles. By carrying out the reaction under the preferred conditions noted above and employing the preferred catalyst yields in the order of from 80 to 86% can be readily realized.

The catalysts useful for effecting reductive alkylation can be a particulate catalytic material in the form of a Group VIII metal such as palladium, platinum, rhodium, nickel, etc. The usual supports for such catalytic materials can be used representative of which include carbon, alumina, silica, etc. The most effective catalyst is 5% palladium on a carbon support. The preferred catalyst as a 50% water wet mixture is employed in the amount of about 1 wt. % based on the total reactor charge.

In order to illustrate to those skilled in the art the best mode contemplated for carrying out the invention, the following working examples are set forth. It is to be understood that these examples are given solely by way of illustration and accordingly, any enumeration of details set forth therein is not to be interpreted as limiting the invention except as such limitations appear in the appended claims. All parts and percentages are by weight unless otherwise noted.

EXAMPLE I

Into a pressure reactor having a capacity of 113.5 liters were charged 23.8 Kg. of ethyl acetate. Hydrazone hydrate (85%) in the amount of 13.9 Kg. was added to the reactor with stirring during a 30 minute period. The reactor was then sealed and heated to 120° C. at 2 atmospheres of pressure. Holding for 5 hours at the indicated temperature resulted in a residual hydrazine content of 0.64%.

To the acetylhydrazide solution were added 0.68 Kg. glacial acetic acid and 0.64 Kg. of catalyst consisting of 5% palladium on carbon support in the form of a 50% water wet mixture. The reaction mixture was pressurized to 10 atmospheres with hydrogen and heated to 90° C. with stirring. Methyl Formcel (54%) in the amount of 28.4 Kg. was continuously pumped into the reactor over a 5 hour period while providing a hydrogen flow rate such as to maintain the pressure at 10 atmospheres. The Methyl Formcel contained 2.5% added glacial acetic acid.

Following the completion of the addition of the formaldehyde, the reaction mixture was cooled and filtered to recover the catalyst. The filtered product was thereupon returned to the reaction vessel and 27.5 Kg. of solvent were removed at 55° C. under reduced pressure to provide 39.3 Kg. of 1,1-dimethyl acetylhydrazide representing about 85% yield of product based on the hydrazine charged.

EXAMPLE II

Into a 2-liter, high-pressure reactor were charged 235.4 g. of methyl laurate, 40 g. of methanol and 59 g. of 85% hydrazine hydrate. The reactor was sealed and with stirring heated to 80° C. and held for 18.5 hours. The reaction was cooled and half of the reactor contents removed, filtered and vacuum dried. The overall yield of lauroyl hydrazide was 93%.

To the remaining portion of lauroyl hydrazide were charged 10 g. of acetic acid, 20 g. of methanol and 5 g. of 5% Pd/C catalyst (50% wet). The reactor was sealed, heated to 95° C. and pressurized to 9 atmospheres of hydrogen. Methyl Formcel (100 g.) was pumped into the reactor over a 0.5 hour period. The reaction was heated for an additional 3.5 hours. The reaction was cooled to ~40° C. and the catalyst removed by filtration. The orange solution was stripped of solvents on a rotoevaporator to yield 138 g. (101%) of crude 1,1-dimethyl lauroylhydrazide. The TLC $R_f$ values of the product agreed with an authentic sample of 1,1-dimethyl lauroyl hydrazide.

EXAMPLE III

Into a 2-liter, high-pressure reactor was charged 243 g. of a benzoyl hydrazide stock solution. The stock solution was prepared by reacting 680.1 g. of methyl benzoate, 288.6 g. of 85% hydrazine hydrate and 100 g. of absolute ethanol and heated for 18 hours at 50° C.

Methanol (1235 g) was added to the pale yellow solution to prevent precipitation of benzoyl hydrazide.

A 5% Pd/C catalyst (3 g. 50% wet) and 5.4 g. of acetic acid were added to the reactor. The reactor was sealed, heated to 82° C. and pressurized with hydrogen to 8.5 atmospheres. Methyl Formcel (65 g.) was pumped into the reactor during a 0.25 hour period. The reaction was heated for an additional 2 hours. The reactor was cooled and vented and the catalyst removed by filtration through Hyflow filter aid. The solvents were stripped on a rotoevaporator and the residue oil was distilled at 118° C. at 0.03 mm. A yield of 56 g. (68% based on hydrazine) of 1,1-dimethylbenzoyl hydrazide was recovered.

EXAMPLE IV

Into a 2-liter Parr reactor were charged 234 g. of a 47.5% solution of acetylhydrazine in methanol, 18 g. of 5% palladium on carbon (50% wet) and 11 g. of glacial acetic acid. The reactor was sealed and heated to 75° C. with stirring. The reactor was purged three times with hydrogen and then pressurized with the hydrogen to 10 atmospheres. A solution of 139 g. of acetaldehyde and 140 g. of isopropanol was pumped into the reactor at a rate of 192 ml/hour. A change in pressure was noted after 10 minutes of the addition. A constant flow of hydrogen was provided to maintain the pressure at 10 atmospheres. After 6 hours total reaction time the reactor was cooled and vented. The product was filtered and vacuum stripped to 130 g. of a light viscosity liquid. TLC and IR analysis indicated that approximately 50% of the acetylhydrazine was converted into diethylacetylhydrazide.

What is claimed is:

1. A method for the preparation of an N,N-dialkyl acid hydrazide of the formula:

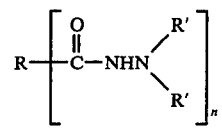

wherein $n$ is the integer 1 or 2; R is alkylene, m-phenylene or p-phenylene when $n$ is 2; R is alkyl or aryl when $n$ is 1; R' is lower alkyl; which comprises the steps:
 a. reacting hydazine with a lower alkyl ester of a carboxylic acid of the formula $R-[COOH]_n$ wherein R and n have the above-defined meanings to form the corresponding unsubstituted acyl hydrazine;
 b. adjusting the pH of the reaction mixture of step (a) to not in excess of 7.5, and thereupon slowly and continuously adding at least 2 moles of a $C_1$-$C_6$ aldehyde for each equivalent of acyl hydrazine formed in step (a) in the presence of hydrogen and a Group VIII metal catalyst while maintaining the reaction temperature at from about 40° to 100° C.; and
 c. recovering said dialkyl acid hydrazide from the reaction mixture of step (b).

2. A process in accordance with claim 1 wherein said hydrogenation catalyst is palladium supported on carbon.

3. A process in accordance with claim 2 wherein from 2 to 3 moles of the aldehyde is added in step (b) per equivalent of the acyl hydrazine formed in step (a).

4. A process in accordance with claim 3 wherein said aldehyde is formaldehyde.

5. A process in accordance with claim 4 wherein the reductive methylation step is effected at a temperature of from 60-85° C. and at a pH of from 6-7.

6. A process in accordance with claim 5 wherein 2.1 moles of formaldehyde is added in step (b) per equivalent of the acyl hydrazine formed in step (a).

* * * * *

UNITED STATES PATENT AND TRADEMARK OFFICE
Certificate

Patent No. 4,071,554                                          Patented January 31, 1978

Robert A. Grimm, Neil A. Randen and Christopher A. Demas

Application having been made by Robert A. Grimm, Neil A. Randen and Christopher A. Demas, the inventors named in the patent above identified, and Ashland Oil, Inc., Ashland, Ky., a corporation of Ky., the assignee, for the issuance of a certificate under the provisions of Title 35, Section 256, of the United States Code, deleting the name of Christopher A. Demas as a joint inventor, and a showing and proof of facts satisfying the requirements of the said section having been submitted, it is this 11th day of August 1981, certified that the name of the said Christopher A. Demas is hereby deleted from the said patent as a joint inventor with the said Robert A. Grimm and Neil A. Randen.

Fred W. Sherling
*Associate Solicitor.*